US011150729B2

(12) United States Patent
Rao et al.

(10) Patent No.: US 11,150,729 B2
(45) Date of Patent: *Oct. 19, 2021

(54) OFF-AXIS GAZE TRACKING IN IN-VEHICLE COMPUTING SYSTEMS

(71) Applicant: Harman International Industries, Incorporated, Stamford, CT (US)

(72) Inventors: Rashmi Rao, West Bloomfield, MI (US); John B. Baluch, Madison Heights, MI (US)

(73) Assignee: Harman International Industries, Incorporated, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/899,369

(22) Filed: Jun. 11, 2020

(65) Prior Publication Data

US 2020/0301507 A1 Sep. 24, 2020

Related U.S. Application Data

(63) Continuation of application No. 16/063,986, filed as application No. PCT/US2017/012204 on Jan. 4, 2017, now Pat. No. 10,712,816.

(Continued)

(51) Int. Cl.
*G06F 3/01* (2006.01)
*A61B 3/113* (2006.01)
(Continued)

(52) U.S. Cl.
CPC ............. *G06F 3/013* (2013.01); *A61B 3/113* (2013.01); *B60K 35/00* (2013.01); *B60Q 3/76* (2017.02); *G06K 9/00597* (2013.01); *G06K 9/00604* (2013.01); *G06K 9/00845* (2013.01); *B60K 2370/73* (2019.05)

(58) Field of Classification Search
CPC ........ G06F 3/013; B60Q 3/76; G06K 9/00597
See application file for complete search history.

(56) References Cited

U.S. PATENT DOCUMENTS 7,199,767 B2 4/2007 Spero
8,885,882 B1 11/2014 Yin et al.
(Continued)

FOREIGN PATENT DOCUMENTS

WO 2014072827 A2 5/2014

OTHER PUBLICATIONS

ISA United States Patent and Trademark Office, International Search Report and Written Opinion Issued in Application No. PCT/US2017/012204, dated Mar. 24, 2017, WIPO, 10 pages.

*Primary Examiner* — Kevin M Nguyen
(74) *Attorney, Agent, or Firm* — McCoy Russell LLP

(57) ABSTRACT

Embodiments are disclosed for gaze tracking with an in-vehicle computing system. In one example, an in-vehicle computing system of a vehicle includes a camera, a light source, a display, a processor, and a storage device storing instructions executable to direct light from the light source to an eye of one or more occupants of the vehicle, receive, at the camera, light reflected from the eye of the one or more occupants of the vehicle, determine a gaze direction of each of the one or more occupants of the vehicle, and operate one or more of the in-vehicle computing system and another vehicle system based on the determined gaze direction.

20 Claims, 7 Drawing Sheets

Related U.S. Application Data

(60) Provisional application No. 62/274,669, filed on Jan. 4, 2016.

(51) Int. Cl.
*G06K 9/00* (2006.01)
*B60Q 3/76* (2017.01)
*B60K 35/00* (2006.01)

(56) References Cited

U.S. PATENT DOCUMENTS

| | | |
|---|---|---|
| 10,712,816 B2 * | 7/2020 | Rao .................. G06F 3/013 |
| 2004/0061831 A1 | 4/2004 | Aughey et al. |
| 2007/0076958 A1 | 4/2007 | Venkatesh |
| 2011/0176003 A1 | 7/2011 | Higgins-Luthman et al. |
| 2012/0274734 A1 | 11/2012 | Byers |
| 2013/0063340 A1 | 3/2013 | Mondragon et al. |
| 2014/0204193 A1 | 7/2014 | Zhang et al. |
| 2015/0029013 A1 | 1/2015 | Osornio Lopez et al. |
| 2016/0085301 A1 * | 3/2016 | Lopez .................. H04N 13/128 345/156 |
| 2016/0119527 A1 | 4/2016 | Shahid et al. |

* cited by examiner

OFF-AXIS GAZE TRACKING IN IN-VEHICLE COMPUTING SYSTEMS

CROSS REFERENCE TO RELATED APPLICATIONS

The present application is a continuation of U.S. Non-Provisional patent application Ser. No. 16/063,986, entitled "OFF-AXIS GAZE TRACKING IN IN-VEHICLE COMPUTING SYSTEMS", and filed on Jun. 19, 2018. U.S. Non-Provisional patent application Ser. No. 16/063,986 is a National Phase of International Patent Application No. PCT/US17/12204, entitled "OFF-AXIS GAZE TRACKING IN IN-VEHICLE COMPUTING SYSTEMS", and filed on Jan. 4, 2017. International Patent Application No. PCT/US17/12204 claims priority to U.S. Provisional Application No. 62/274,669, entitled "OFF-AXIS GAZE TRACKING IN IN-VEHICLE COMPUTING SYSTEMS", and filed on Jan. 4, 2016. The entire contents of each of the above-listed application are hereby incorporated by reference for all purposes.

FIELD

The disclosure relates to gaze tracking using an in-vehicle computing system.

BACKGROUND

Gaze tracking provides useful information regarding a target of a user's focus, and may be used to provide input, gauge a user's attention/intent, monitor user behaviors, and/or other information. Some environments may provide particular challenges to gaze tracking. For example, environments with multiple users may provide challenges regarding fields of view of gaze tracking systems, resolving conflicts between tracking multiple users' eyes, and other issues. Environments with constrained spaces may provide these and other challenges, stemming from a limited available positions for gaze tracking elements.

SUMMARY

One example of an environment in which the above challenges may be present includes a vehicle cabin. In order to address these challenges, the present disclosure provides systems and methods for gaze tracking with an in-vehicle computing system. Embodiments are disclosed for gaze tracking with an in-vehicle computing system. In one example, an in-vehicle computing system of a vehicle includes a camera, a light source, a display, a processor, and a storage device storing instructions executable to direct light from the light source to an eye of one or more occupants of the vehicle, receive, at the camera, light reflected from the eye of the one or more occupants of the vehicle, determine a gaze direction of each of the one or more occupants of the vehicle, and operate one or more of the in-vehicle computing system and another vehicle system based on the determined gaze direction.

BRIEF DESCRIPTION OF THE DRAWINGS

The disclosure may be better understood from reading the following description of non-limiting embodiments, with reference to the attached drawings, wherein below.

DETAILED DESCRIPTION

Figure 1:
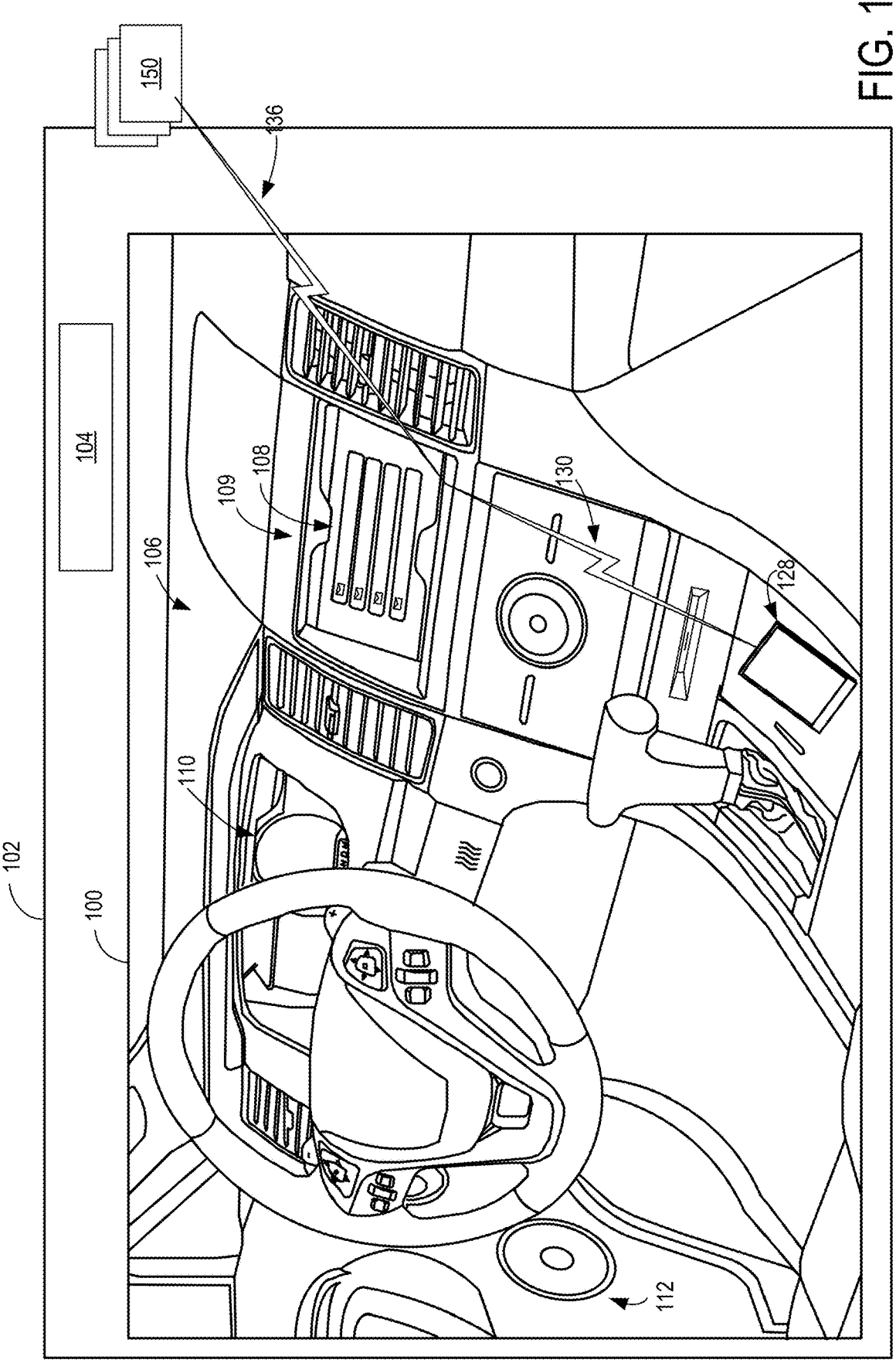
FIG. 1 shows an example partial view of a vehicle cabin in accordance with one or more embodiments of the present disclosure.

FIG. 1 shows an example partial view of one type of environment for a gaze tracking system: an interior of a cabin 100 of a vehicle 102, in which a driver and/or one or more passengers may be seated. Vehicle 102 of FIG. 1 may be a motor vehicle including drive wheels (not shown) and an internal combustion engine 104. Vehicle 102 may be a leading vehicle or a trailing vehicle. Internal combustion engine 104 may include one or more combustion chambers which may receive intake air via an intake passage and exhaust combustion gases via an exhaust passage. Vehicle 102 may be a road automobile, among other types of vehicles. In some examples, vehicle 102 may include a hybrid propulsion system including an energy conversion device operable to absorb energy from vehicle motion and/or the engine and convert the absorbed energy to an energy form suitable for storage by an energy storage device. Vehicle 102 may include a fully electric vehicle, incorporating fuel cells, solar energy capturing elements, and/or other energy storage systems for powering the vehicle.

As shown, an instrument panel 106 may include various displays and controls accessible to a driver (also referred to as the user) of vehicle 102. For example, instrument panel 106 may include a touch screen 108 of an in-vehicle computing system 109 (e.g., an infotainment system), an audio system control panel, and an instrument cluster 110. While the example system shown in FIG. 1 includes audio system controls that may be performed via a user interface of in-vehicle computing system 109, such as touch screen 108 without a separate audio system control panel, in other embodiments, the vehicle may include an audio system control panel, which may include controls for a conventional vehicle audio system such as a radio, compact disc player, MP3 player, etc. The audio system controls may include features for controlling one or more aspects of audio output via speakers 112 of a vehicle speaker system. For example, the in-vehicle computing system or the audio system controls may control a volume of audio output, a distribution of sound among the individual speakers of the vehicle speaker system, an equalization of audio signals, and/or any other aspect of the audio output. In further examples, in-vehicle computing system 109 may adjust a radio station selection, a playlist selection, a source of audio input (e.g., from radio or CD or MP3), etc., based on user input received directly via touch screen 108, or based on data regarding the user (such as a physical state and/or environment of the user) received via external devices 150 and/or mobile device 128.

In some embodiments, one or more hardware elements of in-vehicle computing system 109, such as touch screen 108, a display screen, various control dials, knobs and buttons, memory, processor(s), and any interface elements (e.g., connectors or ports) may form an integrated head unit that is installed in instrument panel 106 of the vehicle. The head unit may be fixedly or removably attached in instrument panel 106. In additional or alternative embodiments, one or more hardware elements of the in-vehicle computing system may be modular and may be installed in multiple locations of the vehicle.

The cabin 100 may include one or more sensors for monitoring the vehicle, the user, and/or the environment. For example, the cabin 100 may include one or more seat-mounted pressure sensors configured to measure the pressure applied to the seat to determine the presence of a user, door sensors configured to monitor door activity, humidity sensors to measure the humidity content of the cabin, microphones to receive user input in the form of voice commands, to enable a user to conduct telephone calls, and/or to measure ambient noise in the cabin 100, etc. It is to be understood that the above-described sensors and/or one or more additional or alternative sensors may be positioned in any suitable location of the vehicle. For example, sensors may be positioned in an engine compartment, on an external surface of the vehicle, and/or in other suitable locations for providing information regarding the operation of the vehicle, ambient conditions of the vehicle, a user of the vehicle, etc. Information regarding ambient conditions of the vehicle, vehicle status, or vehicle driver may also be received from sensors external to/separate from the vehicle (that is, not part of the vehicle system), such as sensors coupled to external devices 150 and/or mobile device 128.

Cabin 100 may also include one or more user objects, such as mobile device 128, that are stored in the vehicle before, during, and/or after travelling. The mobile device 128 may include a smart phone, a tablet, a laptop computer, a portable media player, and/or any suitable mobile computing device. The mobile device 128 may be connected to the in-vehicle computing system via communication link 130. The communication link 130 may be wired (e.g., via Universal Serial Bus [USB], Mobile High-Definition Link [MHL], High-Definition Multimedia Interface [HDMI], Ethernet, etc.) or wireless (e.g., via BLUETOOTH, WIFI, WIFI direct Near-Field Communication [NFC], cellular connectivity, etc.) and configured to provide two-way communication between the mobile device and the in-vehicle computing system. The mobile device 128 may include one or more wireless communication interfaces for connecting to one or more communication links (e.g., one or more of the example communication links described above). The wireless communication interface may include one or more physical devices, such as antenna(s) or port(s) coupled to data lines for carrying transmitted or received data, as well as one or more modules/drivers for operating the physical devices in accordance with other devices in the mobile device. For example, the communication link 130 may provide sensor and/or control signals from various vehicle systems (such as vehicle audio system, climate control system, etc.) and the touch screen 108 to the mobile device 128 and may provide control and/or display signals from the mobile device 128 to the in-vehicle systems and the touch screen 108. The communication link 130 may also provide power to the mobile device 128 from an in-vehicle power source in order to charge an internal battery of the mobile device.

In-vehicle computing system 109 may also be communicatively coupled to additional devices operated and/or accessed by the user but located external to vehicle 102, such as one or more external devices 150. In the depicted embodiment, external devices are located outside of vehicle 102 though it will be appreciated that in alternate embodiments, external devices may be located inside cabin 100. The external devices may include a server computing system, personal computing system, portable electronic device, electronic wrist band, electronic head band, portable music player, electronic activity tracking device, pedometer, smartwatch, GPS system, etc. External devices 150 may be connected to the in-vehicle computing system via communication link 136 which may be wired or wireless, as discussed with reference to communication link 130, and configured to provide two-way communication between the external devices and the in-vehicle computing system. For example, external devices 150 may include one or more sensors and communication link 136 may transmit sensor output from external devices 150 to in-vehicle computing system 109 and touch screen 108. External devices 150 may also store and/or receive information regarding contextual data, user behavior/preferences, operating rules, etc. and may transmit such information from the external devices 150 to in-vehicle computing system 109 and touch screen 108.

In-vehicle computing system 109 may analyze the input received from external devices 150, mobile device 128, and/or other input sources and select settings for various in-vehicle systems (such as climate control system or audio system), provide output via touch screen 108 and/or speakers 112, communicate with mobile device 128 and/or external devices 150, and/or perform other actions based on the assessment. In some embodiments, all or a portion of the assessment may be performed by the mobile device 128 and/or the external devices 150. In some embodiments, the external devices 150 may include in-vehicle computing devices of another vehicle, as such the vehicle may be a vehicle leading the vehicle 102, or may be a vehicle trailing behind vehicle 102.

In some embodiments, one or more of the external devices 150 may be communicatively coupled to in-vehicle computing system 109 indirectly, via mobile device 128 and/or another of the external devices 150. For example, communication link 136 may communicatively couple external devices 150 to mobile device 128 such that output from external devices 150 is relayed to mobile device 128. Data received from external devices 150 may then be aggregated at mobile device 128 with data collected by mobile device 128, the aggregated data then transmitted to in-vehicle computing system 109 and touch screen 108 via communication link 130. Similar data aggregation may occur at a server system and then transmitted to in-vehicle computing system 109 and touch screen 108 via communication link 136/130.

Figure 2:
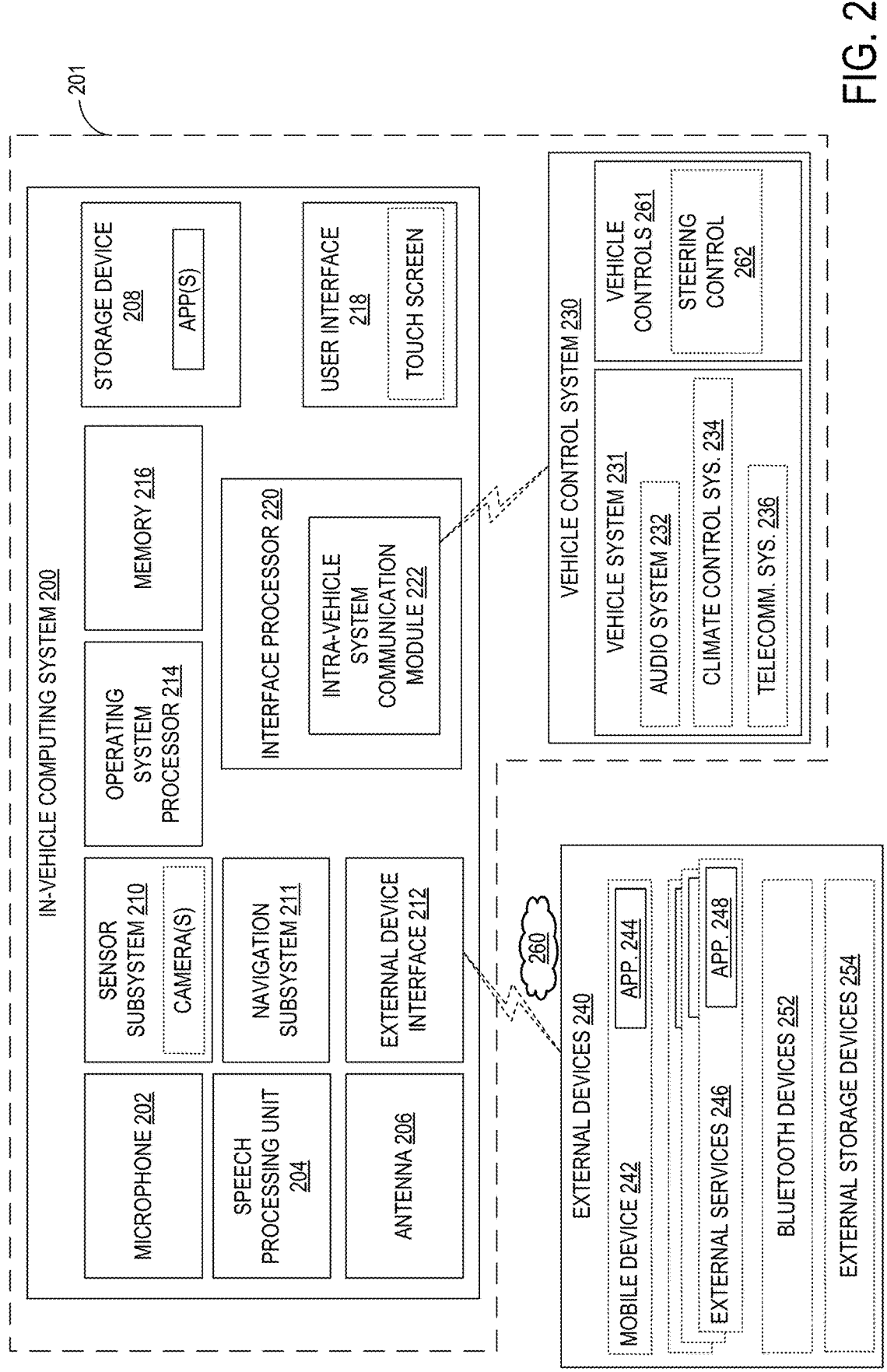
FIG. 2 shows an example in-vehicle computing system in accordance with one or more embodiments of the present disclosure.

FIG. 2 shows a block diagram of an in-vehicle computing system 200 configured and/or integrated inside vehicle 201. In-vehicle computing system 200 may be an example of in-vehicle computing system 109 of FIG. 1 and/or may perform one or more of the methods described herein in some embodiments. In some examples, the in-vehicle computing system may be a vehicle infotainment system configured to provide information-based media content (audio and/or visual media content, including entertainment content, navigational services, etc.) to a vehicle user to enhance the operator's in-vehicle experience. The vehicle infotainment system may include, or be coupled to, various vehicle systems, sub-systems, hardware components, as well as software applications and systems that are integrated in, or integratable into, vehicle 201 in order to enhance an in-vehicle experience for a driver and/or a passenger.

In-vehicle computing system 200 may include one or more processors including an operating system processor 214 and an interface processor 220. Operating system processor 214 may execute an operating system on the in-vehicle computing system, and control input/output, display, playback, and other operations of the in-vehicle computing system. Interface processor 220 may interface with a vehicle control system 230 via an intra-vehicle system communication module 222.

Intra-vehicle system communication module 222 may output data to other vehicle systems 231 and vehicle control elements 261, while also receiving data input from other vehicle components and systems 231, 261, e.g. by way of vehicle control system 230. When outputting data, intra-vehicle system communication module 222 may provide a signal via a bus corresponding to any status of the vehicle, the vehicle surroundings, or the output of any other information source connected to the vehicle. Vehicle data outputs may include, for example, analog signals (such as current velocity), digital signals provided by individual information sources (such as clocks, thermometers, location sensors such as Global Positioning System [GPS] sensors, etc.), digital signals propagated through vehicle data networks (such as an engine controller area network [CAN] bus through which engine related information may be communicated, a climate control CAN bus through which climate control related information may be communicated, and a multimedia data network through which multimedia data is communicated between multimedia components in the vehicle). For example, the in-vehicle computing system may retrieve from the engine CAN bus the current speed of the vehicle estimated by the wheel sensors, a power state of the vehicle via a battery and/or power distribution system of the vehicle, an ignition state of the vehicle, etc. In addition, other interfacing means such as Ethernet may be used as well without departing from the scope of this disclosure.

A non-volatile storage device 208 may be included in in-vehicle computing system 200 to store data such as instructions executable by processors 214 and 220 in non-volatile form. The storage device 208 may store application data to enable the in-vehicle computing system 200 to run an application for connecting to a cloud-based server and/or collecting information for transmission to the cloud-based server. The application may retrieve information gathered by vehicle systems/sensors, input devices (e.g., user interface 218), devices in communication with the in-vehicle computing system (e.g., a mobile device connected via a Bluetooth link), etc. In-vehicle computing system 200 may further include a volatile memory 216. Volatile memory 216 may be random access memory (RAM). Non-transitory storage devices, such as non-volatile storage device 208 and/or volatile memory 216, may store instructions and/or code that, when executed by a processor (e.g., operating system processor 214 and/or interface processor 220), controls the in-vehicle computing system 200 to perform one or more of the actions described in the disclosure.

A microphone 202 may be included in the in-vehicle computing system 200 to receive voice commands from a user, to measure ambient noise in the vehicle, to determine whether audio from speakers of the vehicle is tuned in accordance with an acoustic environment of the vehicle, etc. A speech processing unit 204 may process voice commands, such as the voice commands received from the microphone 202. In some embodiments, in-vehicle computing system 200 may also be able to receive voice commands and sample ambient vehicle noise using a microphone included in an audio system 232 of the vehicle.

One or more additional sensors may be included in a sensor subsystem 210 of the in-vehicle computing system 200. For example, the sensor subsystem 210 may include a camera, such as a rear view camera for assisting a user in parking the vehicle and/or a cabin camera for identifying a user (e.g., using facial recognition and/or user gestures). Sensor subsystem 210 of in-vehicle computing system 200 may communicate with and receive inputs from various vehicle sensors and may further receive user inputs. For example, the inputs received by sensor subsystem 210 may include transmission gear position, transmission clutch position, gas pedal input, brake input, transmission selector position, vehicle speed, engine speed, mass airflow through the engine, ambient temperature, intake air temperature, etc., as well as inputs from climate control system sensors (such as heat transfer fluid temperature, antifreeze temperature, fan speed, passenger compartment temperature, desired passenger compartment temperature, ambient humidity, etc.), an audio sensor detecting voice commands issued by a user, a fob sensor receiving commands from and optionally tracking the geographic location/proximity of a fob of the vehicle, etc. While certain vehicle system sensors may communicate with sensor subsystem 210 alone, other sensors may communicate with both sensor subsystem 210 and vehicle control system 230, or may communicate with sensor subsystem 210 indirectly via vehicle control system 230. A navigation subsystem 211 of in-vehicle computing system 200 may generate and/or receive navigation information such as location information (e.g., via a GPS sensor and/or other sensors from sensor subsystem 210), route guidance, traffic information, point-of-interest (POI) identification, and/or provide other navigational services for the driver.

External device interface 212 of in-vehicle computing system 200 may be coupleable to and/or communicate with one or more external devices 240 located external to vehicle 201. While the external devices are illustrated as being located external to vehicle 201, it is to be understood that they may be temporarily housed in vehicle 201, such as when the user is operating the external devices while operating vehicle 201. In other words, the external devices 240 are not integral to vehicle 201. The external devices 240 may include a mobile device 242 (e.g., connected via a Bluetooth, NFC, WIFI direct, or other wireless connection) or an alternate Bluetooth-enabled device 252. Mobile device 242 may be a mobile phone, smart phone, wearable devices/sensors that may communicate with the in-vehicle computing system via wired and/or wireless communication, or other portable electronic device(s). Other external devices include external services 246. For example, the external devices may include extra-vehicular devices that are separate from and located externally to the vehicle. Still other external devices include external storage devices 254, such as solid-state drives, pen drives, USB drives, etc. External devices 240 may communicate with in-vehicle computing system 200 either wirelessly or via connectors without departing from the scope of this disclosure. For example, external devices 240 may communicate with in-vehicle computing system 200 through the external device interface 212 over network 260, a universal serial bus (USB) connection, a direct wired connection, a direct wireless connection, and/or other communication link.

The external device interface 212 may provide a communication interface to enable the in-vehicle computing system to communicate with mobile devices associated with contacts of the driver. For example, the external device interface 212 may enable phone calls to be established and/or text messages (e.g., SMS, MMS, etc.) to be sent (e.g., via a cellular communications network) to a mobile device associated with a contact of the driver. The external device interface 212 may additionally or alternatively provide a wireless communication interface to enable the in-vehicle computing system to synchronize data with one or more devices in the vehicle (e.g., the driver's mobile device) via WIFI direct, as described in more detail below.

One or more applications 244 may be operable on mobile device 242. As an example, mobile device application 244 may be operated to aggregate user data regarding interactions of the user with the mobile device. For example, mobile device application 244 may aggregate data regarding music playlists listened to by the user on the mobile device, telephone call logs (including a frequency and duration of telephone calls accepted by the user), positional information including locations frequented by the user and an amount of time spent at each location, etc. The collected data may be transferred by application 244 to external device interface 212 over network 260. In addition, specific user data requests may be received at mobile device 242 from in-vehicle computing system 200 via the external device interface 212. The specific data requests may include requests for determining where the user is geographically located, an ambient noise level and/or music genre at the user's location, an ambient weather condition (temperature, humidity, etc.) at the user's location, etc. Mobile device application 244 may send control instructions to components (e.g., microphone, etc.) or other applications (e.g., navigational applications) of mobile device 242 to enable the requested data to be collected on the mobile device. Mobile device application 244 may then relay the collected information back to in-vehicle computing system 200.

Likewise, one or more applications 248 may be operable on external services 246. As an example, external services applications 248 may be operated to aggregate and/or analyze data from multiple data sources. For example, external services applications 248 may aggregate data from one or more social media accounts of the user, data from the in-vehicle computing system (e.g., sensor data, log files, user input, etc.), data from an internet query (e.g., weather data, POI data), etc. The collected data may be transmitted to another device and/or analyzed by the application to determine a context of the driver, vehicle, and environment and perform an action based on the context (e.g., requesting/sending data to other devices).

Vehicle control system 230 may include controls for controlling aspects of various vehicle systems 231 involved in different in-vehicle functions. These may include, for example, controlling aspects of vehicle audio system 232 for providing audio entertainment to the vehicle occupants, aspects of climate control system 234 for meeting the cabin cooling or heating needs of the vehicle occupants, as well as aspects of telecommunication system 236 for enabling vehicle occupants to establish telecommunication linkage with others.

Audio system 232 may include one or more acoustic reproduction devices including electromagnetic transducers such as speakers. Vehicle audio system 232 may be passive or active such as by including a power amplifier. In some examples, in-vehicle computing system 200 may be the only audio source for the acoustic reproduction device or there may be other audio sources that are connected to the audio reproduction system (e.g., external devices such as a mobile phone). The connection of any such external devices to the audio reproduction device may be analog, digital, or any combination of analog and digital technologies.

Climate control system 234 may be configured to provide a comfortable environment within the cabin or passenger compartment of vehicle 201. Climate control system 234 includes components enabling controlled ventilation such as air vents, a heater, an air conditioner, an integrated heater and air-conditioner system, etc. Other components linked to the heating and air-conditioning setup may include a windshield defrosting and defogging system capable of clearing the windshield and a ventilation-air filter for cleaning outside air that enters the passenger compartment through a fresh-air inlet.

Vehicle control system 230 may also include controls for adjusting the settings of various vehicle controls 261 (or vehicle system control elements) related to the engine and/or auxiliary elements within a cabin of the vehicle, such as steering wheel controls 262 (e.g., steering wheel-mounted audio system controls, cruise controls, windshield wiper controls, headlight controls, turn signal controls, etc.), instrument panel controls, microphone(s), accelerator/brake/clutch pedals, a gear shift, door/window controls positioned in a driver or passenger door, seat controls, cabin light controls, audio system controls, cabin temperature controls, etc. Vehicle controls 261 may also include internal engine and vehicle operation controls (e.g., engine controller module, actuators, valves, etc.) that are configured to receive instructions via the CAN bus of the vehicle to change operation of one or more of the engine, exhaust system, transmission, and/or other vehicle system. The control signals may also control audio output at one or more speakers of the vehicle's audio system 232. For example, the control signals may adjust audio output characteristics such as volume, equalization, audio image (e.g., the configuration of the audio signals to produce audio output that appears to a user to originate from one or more defined locations), audio distribution among a plurality of speakers, etc. Likewise, the control signals may control vents, air conditioner, and/or heater of climate control system 234. For example, the control signals may increase delivery of cooled air to a specific section of the cabin.

Control elements positioned on an outside of a vehicle (e.g., controls for a security system) may also be connected to computing system 200, such as via communication module 222. The control elements of the vehicle control system may be physically and permanently positioned on and/or in the vehicle for receiving user input. In addition to receiving control instructions from in-vehicle computing system 200, vehicle control system 230 may also receive input from one or more external devices 240 operated by the user, such as from mobile device 242. This allows aspects of vehicle systems 231 and vehicle controls 261 to be controlled based on user input received from the external devices 240.

In-vehicle computing system 200 may further include an antenna 206. Antenna 206 is shown as a single antenna, but may comprise one or more antennas in some embodiments. The in-vehicle computing system may obtain broadband wireless internet access via antenna 206, and may further receive broadcast signals such as radio, television, weather, traffic, and the like. The in-vehicle computing system may receive positioning signals such as GPS signals via one or more antennas 206. The in-vehicle computing system may also receive wireless commands via RF such as via antenna(s) 206 or via infrared or other means through appropriate receiving devices. In some embodiments, antenna 206 may be included as part of audio system 232 or telecommunication system 236. Additionally, antenna 206 may provide AM/FM radio signals to external devices 240 (such as to mobile device 242) via external device interface 212.

One or more elements of the in-vehicle computing system 200 may be controlled by a user via user interface 218. User interface 218 may include a graphical user interface presented on a touch screen, such as touch screen 108 of FIG. 1, and/or user-actuated buttons, switches, knobs, dials, sliders, etc. For example, user-actuated elements may include steering wheel controls, door and/or window controls, instrument panel controls, audio system settings, climate control system settings, and the like. A user may also interact with one or more applications of the in-vehicle computing system 200 and mobile device 242 via user interface 218. In addition to receiving a user's vehicle setting preferences on user interface 218, vehicle settings selected by in-vehicle control system may be displayed to a user on user interface 218. Notifications and other messages (e.g., received messages), as well as navigational assistance, may be displayed to the user on a display of the user interface. User preferences/information and/or responses to presented messages may be performed via user input to the user interface.

Figure 3:
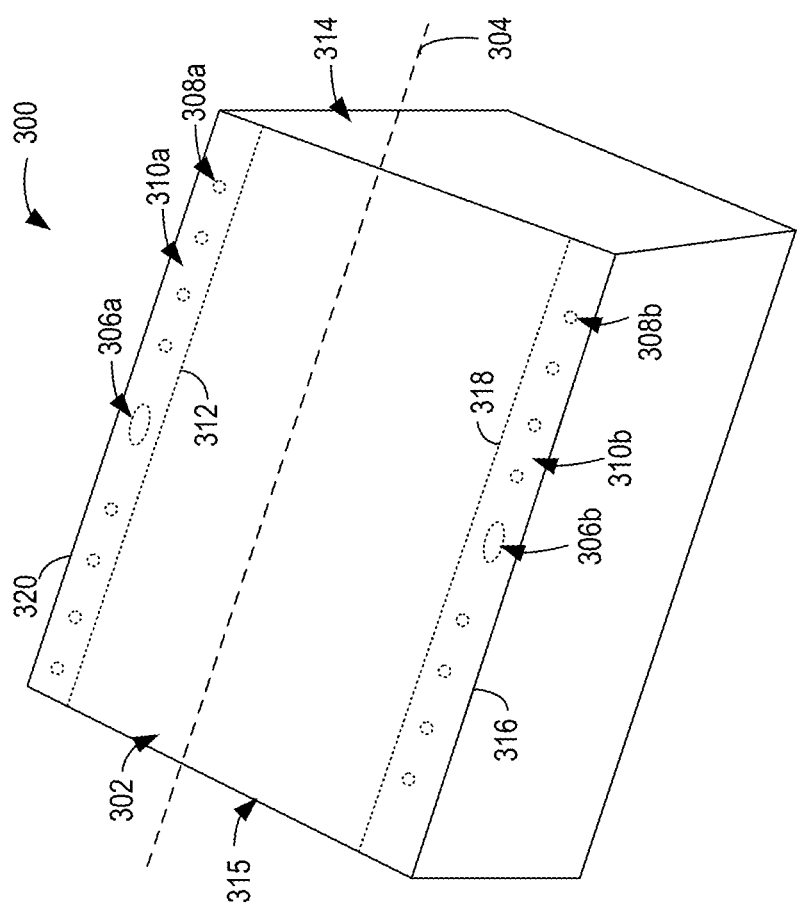
FIG. 3 shows an example head unit including gaze tracking elements in accordance with one or more embodiments of the present disclosure.

FIG. 3 shows an example head unit 300 including gaze tracking elements. Head unit 300 may include, be included/integrated in, and/or be an example of an in-vehicle computing system, such as in-vehicle computing system 109 and/or 200 of FIGS. 1 and 2, respectively. Head unit 300 includes a display 302. Display 302 may be an example of touch screen 108 of FIG. 1. Gaze tracking elements may be positioned on either a top or a bottom of the display 302. Gaze tracking elements may be positioned on a topmost end (e.g., starting from a top edge of display 302) and/or a bottommost end (e.g., starting from a bottom edge of display 302) relative to a longitudinal axis 304.

In a first example, gaze tracking elements may include a gaze tracking camera 306a and one or more gaze tracking light sources 308a positioned in a component region 310a. The gaze tracking camera 306a may include a depth camera, an infrared camera, an RGB camera, and/or any other suitable imaging device for capturing images of one or more users' eyes. The camera may be configured to capture images of the whole eye, part of the eye (e.g., pupil tracking, retina tracking, etc.), and/or head position in order to determine a gaze direction of the user.

The gaze tracking light sources 308a may include infrared light sources (e.g., infrared light-emitting diodes [LEDs]), white LEDs, and/or any other suitable light source for projecting light toward one or more users' eyes. Infrared light sources may be used to allow the gaze tracking system to operate in low light situations (e.g., driving at night). In some examples, the light directed toward the one or more users' eyes may be referred to as glint and the light sources may be referred to as glint sources. The number and placement of light sources 308a is exemplary in nature, and any suitable number and position of light sources may be used to achieve a specified light coverage region. For example, the number and position of light sources may be selected to ensure that all areas of a vehicle cabin receive light from the light sources and/or a driver/passenger region of the cabin receives light from the light sources. In some examples, the light sources 308a may be tracking light sources. For example, one or more of the light sources 308a may be moveable (e.g., automatically via an actuator) based on one or more conditions. For example, camera 306a and/or other sensors may be used to detect or estimate a position of one or more users within the vehicle, and the one or more tracking light sources may be automatically moved to direct light toward the detected/estimated position of the one or more users. One or more of the light sources 308a may be stationary in additional or alternative examples.

In the first example, the top edge of the display coincides with the bottom edge of the component region 310a, designated by dashed line 312. The bottom edge of the display in the first example coincides with the bottom edge of head unit electronics housing 314, designated by solid line 316. Housing 314 may house cabling/connectors, circuit boards, power supplies, and/or any other suitable electronics utilized by the display, gaze-tracking camera, and/or light source(s). In some examples, housing 314 may additionally house one or more processing units, memory, and/or other components of an in-vehicle computing system such as those described above with respect to FIG. 2. One or more electronic components for head unit 300 may additionally or alternatively be located outside of housing 314 and/or coupled to housing 314.

In a second example, gaze tracking elements may include a gaze tracking camera 306b and one or more gaze tracking light sources 308b positioned in a component region 310b. The gaze tracking elements described with respect to this second example correspond to those described above with respect to the first example. In other words, the description of camera 306a applies to camera 306b, the description of light sources 308a applies to light sources 308b, and the description of component region 310a applies to 310b. The only difference in these pairs of components is the relative positioning at the top/bottom of display 302. In this second example, camera 306b, light sources 308b, and component region 310b are positioned at a bottom end of display 302 relative to the longitudinal axis 304. In this example, the bottom edge of display 302 corresponds to the top edge of the component region 310b, designated by dashed line 318. The top edge of display 302 in this example corresponds to the top edge of housing 314, designated by solid line 320.

In a third example, both sets of cameras 306a/b, light sources 308a/b, and component regions 310a/b may be utilized. In this third example, display 302 may extend from the bottom edge of component region 310a (e.g., dashed line 312) to the top edge of component region 310b (e.g., dashed line 318).

In the illustrated example, the housing 314 may be rectangular in shape. In other examples, the housing 314 may have other shapes. A front surface 315 of the housing 314 may be covered by an at least partially transparent structure, such as a sheet of glass, acrylic, plastic, and/or other at least partially transparent material. The at least partially transparent structure may cover (e.g., the entirety of or a portion of) the front surface 315 of the housing 314 (e.g., the display 302, the camera 306a/b, the light sources 308a/b, etc.). In some examples, the at least partially transparent structure may extend past the front surface of the housing, and cover additional components in a central console region of a vehicle. The at least partially transparent structure may have a different shape than the housing 314 and/or the same shape as the housing 314.

The positioning of gaze tracking components in any of the above-described examples may provide a usage range, defined as the distance between the sensor (e.g., the gaze tacking camera 306a and/or 306b) and the target or targets' eyes, is large enough to accommodate a target of any height and leg length. The field of view of the camera(s) may be wide enough so that both the driver's and the passenger's eyes can be seen by the system concurrently under normal operating conditions. Example configurations may include a field of view of 35-40 degrees, a 6-12 mm lens, and the use of an infrared filter in order to achieve the above features.

Figure 4:
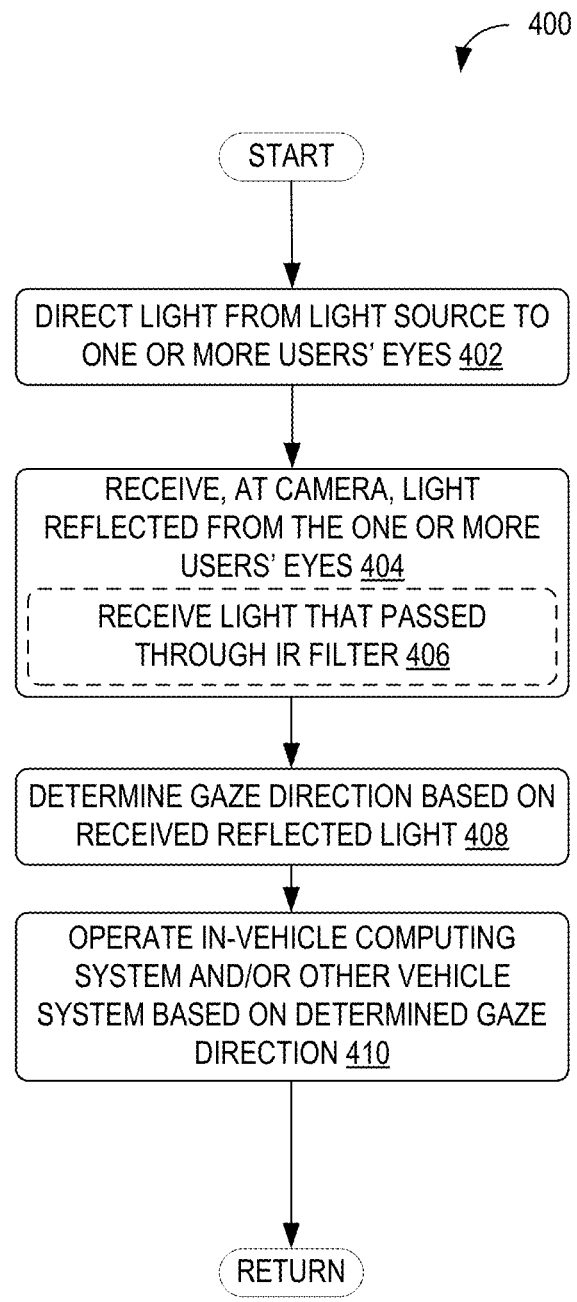
FIG. 4 is a flow chart for a method of performing gaze tracking in accordance with one or more embodiments of the present disclosure.

FIG. 4 is a flow chart of a method 400 for detecting one or more users' gaze(s). Method 400 may be performed by any suitable computing device, including in-vehicle computing device 109/200 of FIGS. 1-2 and/or head unit 300 of FIG. 3. For example, the gaze tracking components described in method 400 may correspond to those described above with respect to FIG. 3. At 402, the method includes directing light from a light source to one or more users' eyes. For example, the light may include infrared light, and the light sources may be positioned as described above with respect to light sources 308a and/or 308b of FIG. 3.

At 404, the method includes receiving, at a camera, light reflected from the one or more users' eyes. For example, the reflected light may be received at a camera such as gaze tracking camera 306a and/or 306b of FIG. 3. As indicated at 406, the received light may include light that has reflected off the one or more users' eyes (e.g., off the one or more users' pupils) and then passed through an infrared filter to filter out/remove ambient light. At 408, the method includes determining gaze direction based on the received reflected light. For example, the gaze direction may be determined based on a direction at which the incoming reflected light impinged on a sensor element of the camera and/or the position of the pixel(s) of the sensor that received the reflected light. A processor of the in-vehicle computing system may determine the gaze direction based on this sensor data.

At 410, the method includes operating the in-vehicle computing system and/or other vehicle system based on the determined gaze direction. For example, the gaze direction may be used to indicate a selection of an item displayed on a display of the in-vehicle computing system. In another example, the gaze direction may indicate that the attention of the driver is directed away from the road, which may cause the in-vehicle computing system to output an alert (e.g., an audio alert via vehicle speakers and/or a visual alert via the display of the in-vehicle computing system). Any suitable control may be performed based on the gaze direction, including controlling actuators, output devices, and the like. In some examples, the gaze direction may be stored in vehicle memory (e.g., memory of the in-vehicle computing system) and an action may be taken at a later time based on an analysis of historical gaze tracking data.

For example, a gaze direction of both a passenger and a driver may be detected by execution of method 400. One or both of the gaze directions and/or the sensor data used to determine the gaze directions may be stored in order to evaluate each gaze direction independently. Where conflicts arise (e.g., both the driver and passenger have gaze directions that select different user interface options on a display in the vehicle), the in-vehicle computing system may take measures to resolve such conflicts. For example, a driver gaze direction may be analyzed and/or acted upon first in order to ensure that the driver maintains control of the vehicle. In other examples, a prompt may be displayed in order to alert the driver/passenger to the conflict and allow the driver/passenger to confirm an action to be taken. Any suitable conflict resolution may be applied in order to address the issues arising from determining multiple gaze directions concurrently and/or in a coordinated manner.

Figure 5:
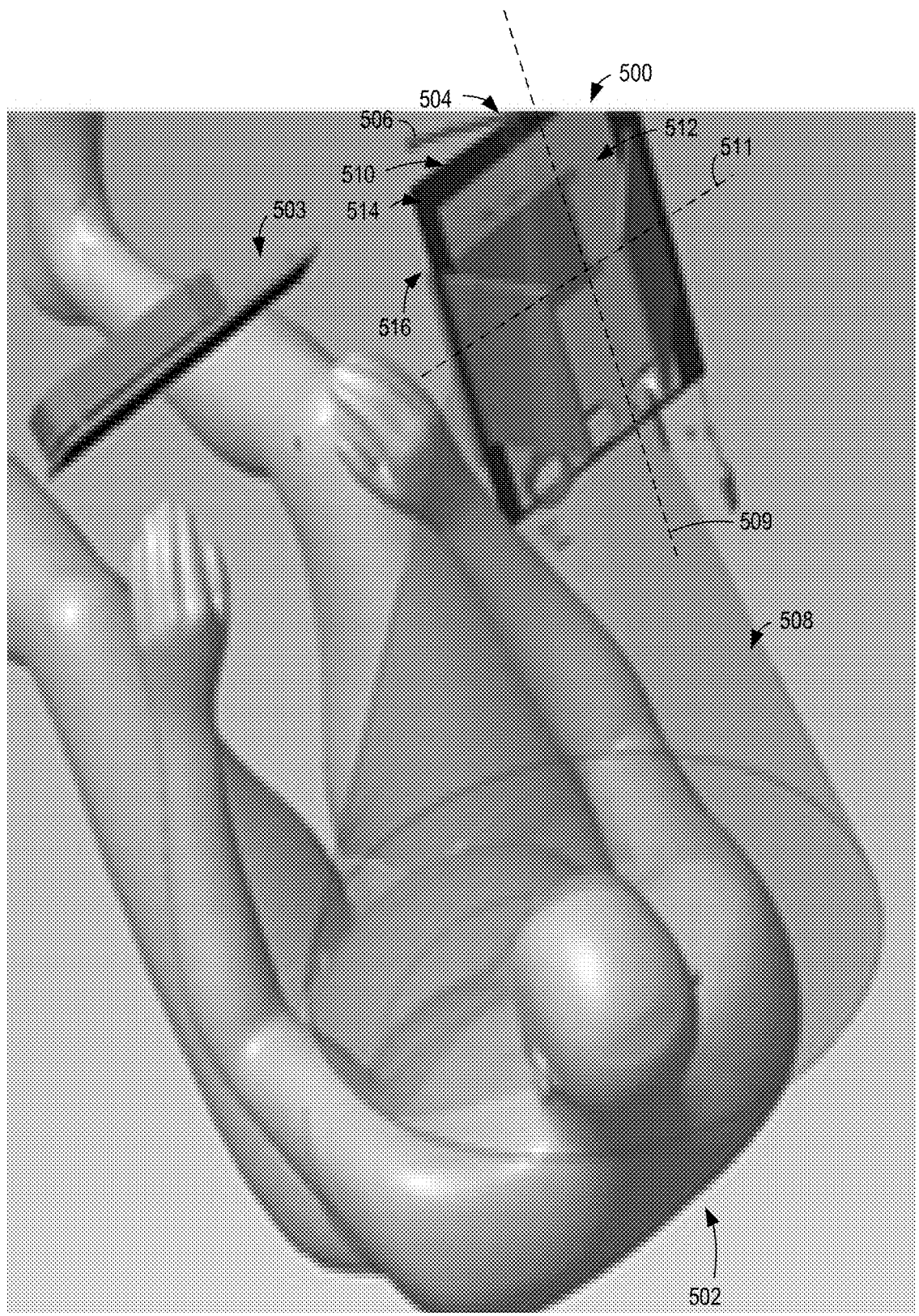
FIGS. 5-7 show different views of an example head unit positioned relative to a driver of a vehicle in accordance with one or more embodiments of the present disclosure.
Figure 6:
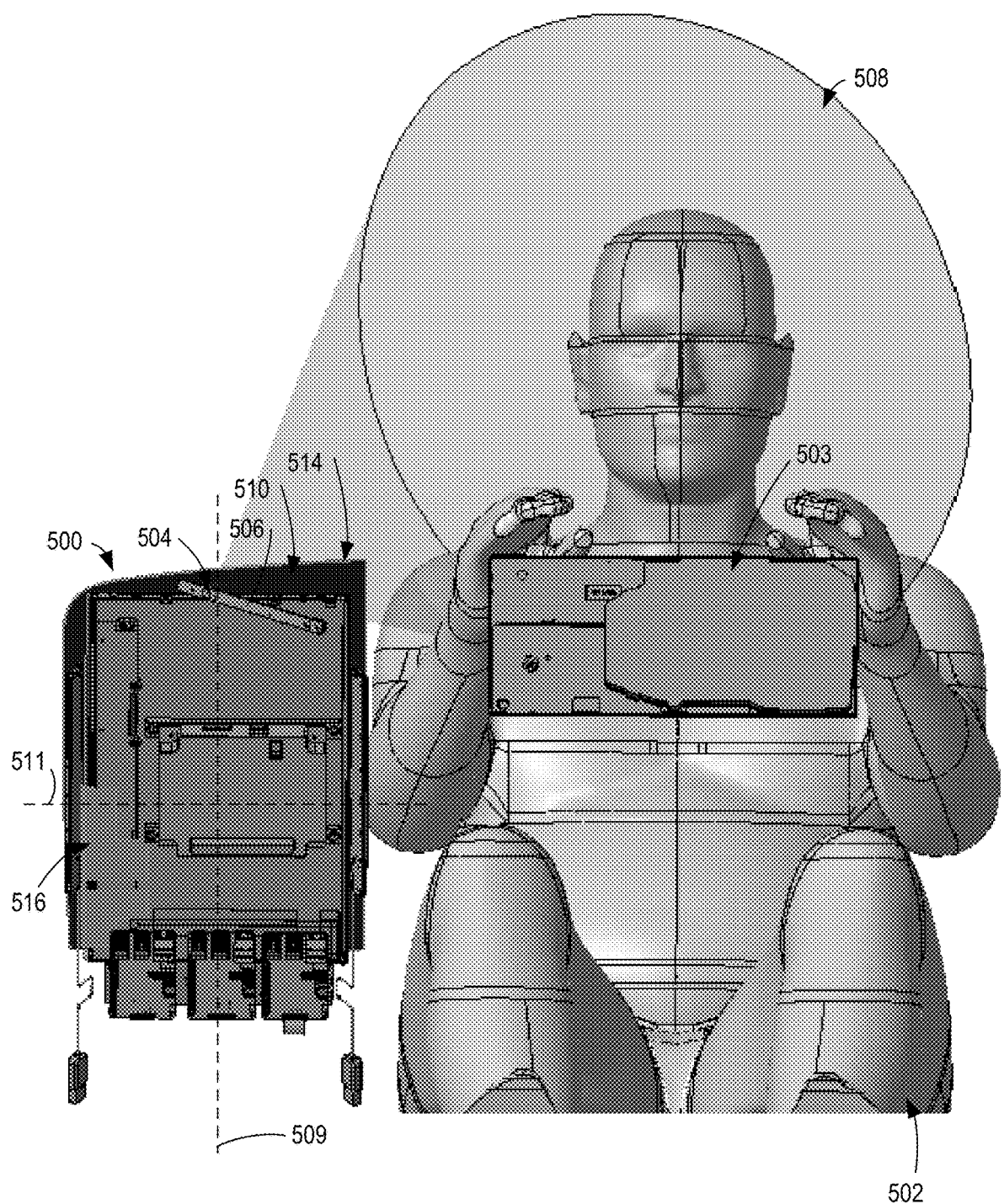
Figure 7:
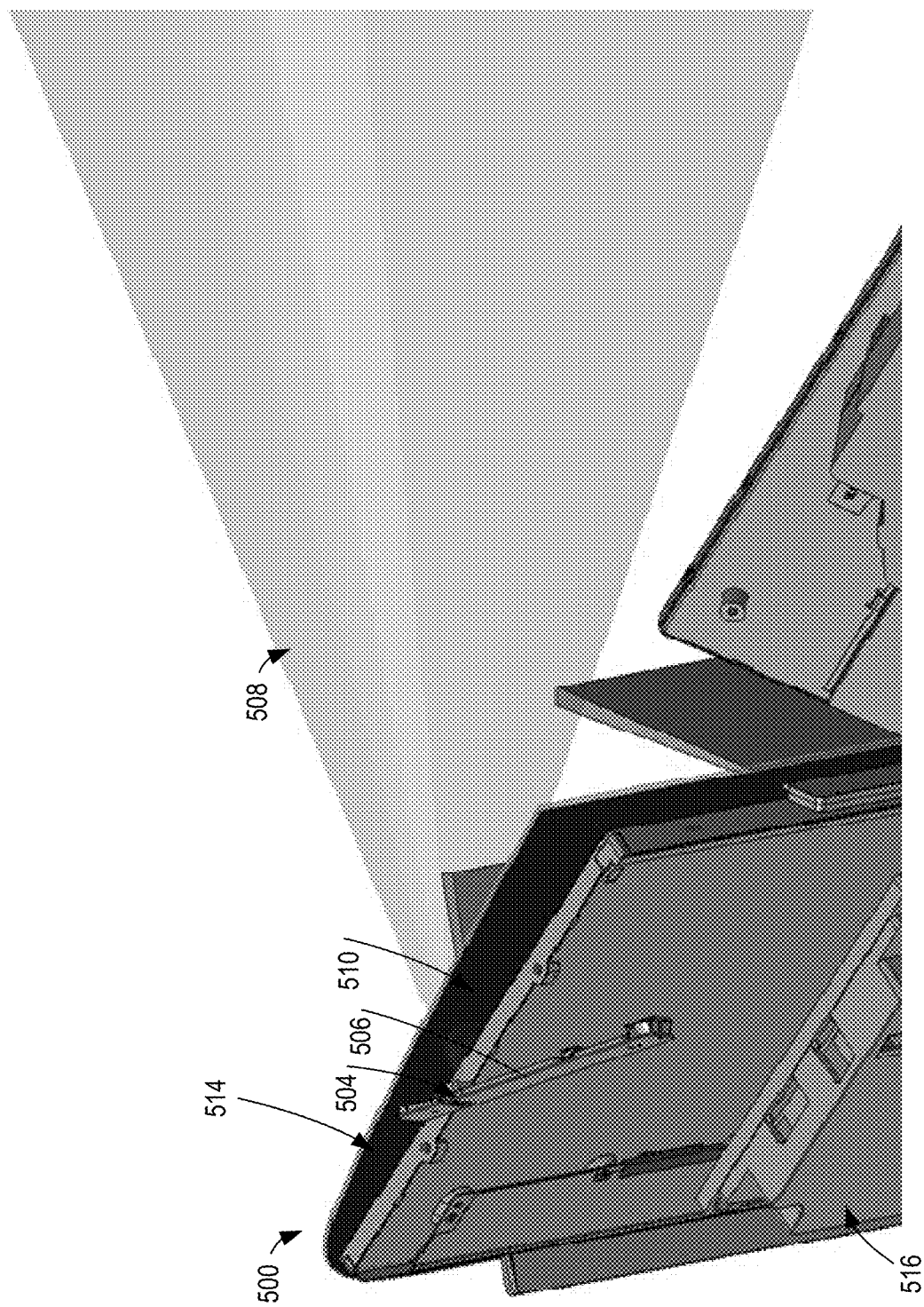

FIGS. 5-7 show different views of an example head unit 500 positioned to a side of a driver 502 of a vehicle. For example, the head unit 500 may be positioned in a center console region of a vehicle, to a side of an instrument cluster 503 positioned in front of the driver 502. In FIG. 5, an eye tracker 504 for the head unit 500 is shown located on an angled extension arm 506 to position the eye tracker at a particular angled location relative to the driver 502 (e.g., relative to a seat in which the driver is likely to be positioned while operating the vehicle) to maximize the eye box and/or eye box cone 508 (e.g., the region in which the driver's eyes may be tracked, or the field of view of the eye tracker) of the driver. In this way, the eye tracker may be positioned outside a line of sight of a driver or other occupant of the vehicle, and still be able to detect a gaze of the driver/occupant. The angled extension arm 506 may be angled relative to other components of the head unit. For example, the angled extension arm 506 may be angled (e.g., approximately 70 degrees in the illustrated example) relative to a longitudinal axis 509 and/or angled (e.g., approximately 20 degrees in the illustrated example) relative to a transverse axis 511 that is perpendicular to the longitudinal axis 509.

In order to illuminate the driver (e.g., the driver's eyes) for detection, one or more illumination light sources 510 may be positioned above (or below, in other examples) a center display 512 of the head unit 500. The light sources 510 may include visible light sources configured to emit visible light and/or infrared light sources configured to emit infrared light (e.g., for depth sensing). The light sources 510 may be positioned and/or angled to illuminate at least a portion of the eye box cone 508, at least the entire eye box cone 508, and/or only the eye box cone 508. In some examples, the light sources 510 may be configured to illuminate the eyes of occupants that are outside of the line of sight of the eye tracker. For example, the light sources may be positioned separately from the eye tracker (e.g., in a location that enables the light sources to directly transmit light to the eyes of the occupants without any intervening elements), and/or the light sources may direct light toward one or more redirecting optical elements having a structure and positioned in a location that enables the optical elements to redirect light from the light sources to the eyes of the occupants. In additional or alternative examples, the light sources 510 may be configured to illuminate the eyes of occupants, even when the eye tracker and/or light sources are out of the line of sight of the occupants. In some examples, one or more of the light sources 510 may be positioned on the angled extension arm 506. In such examples, or in alternative examples, one or more of the light sources 510 may be additionally or alternatively positioned along a bezel of the display 512 (e.g., separate from and/or in front of the angled extension arm 506). The bezel may be integrated into a cover glass 514 or separate from and positioned behind the cover glass and around the display 512. The bezel and cover glass 514 may have a same or different shape than the housing of head unit 500. For example, the cover glass 514 may extend below a bottom edge of the housing of head unit 500.

The head unit 500 may include a circuit board or other substrate for mounting electrical components of the head unit (e.g., display components, imaging components, processors, memory, power supplies, etc.). In some examples, the circuit board or other substrate may form a rear 516 of the head unit 500 (shown in more detail in the view of FIGS. 6 and 7) and/or may be surrounded by the bezel of the display. In additional or alternative examples, the rear 516 of the head unit 500 may be formed by a rear surface of a housing for the electrical components and/or circuit board/substrate. The angled extension arm 506 may be mounted to the rear 516 of the head unit 500 (e.g., to the circuit board/substrate and/or to the rear surface of the housing) at at least one position along the arm, and may extend above the rear of the head unit (e.g., the circuit board/substrate and/or the housing). In some examples, the eye tracker 504 (e.g., an image sensor) may include and/or be positioned relative to image optics configured to collect light from the environment (e.g., in a region of the driver 502 and/or within the eye box cone 508) and direct the light to the eye tracker (e.g., the image sensor) to increase a signal-to-noise ratio of incoming light (e.g., to maximize reflected light that is detected by the eye tracker versus ambient light).

The integration of gaze-tracking into vehicle infotainment head units (e.g., head unit 300 of FIG. 3 and/or head unit 500 of FIG. 4) may enable the system to utilize the location of the head unit within a vehicle cabin to achieve the usage range and field of view described above. The hardware related to gaze-tracking may be located in the center-stack of the vehicle either above or below the display, and integrated into the same package as the head-unit. The camera (e.g., camera 306*a* and/or 306*b* of FIG. 3) may be off-axis from the driver's and the passenger's eyes (e.g., out of a line-of-sight of the driver and/or passenger), and may still identify the location of either party's gaze when configured as described above. In this way, it may not be necessary to position the device in front of the user or to re-position the camera before use, which has a technical effect of increasing the ease of use of the system. Such a lack of re-positioning may also have a technical effect of decreasing the amount of time for initializing the gaze tracking system, enabling the system to be started earlier than gaze tracking systems with other arrangements. In some examples, the positioning of the components may enable smaller eye tracker transmitters (e.g., light sources) and/or receivers (e.g., image sensors) to be used. For example, an array of transmitters and/or receivers of a first, smaller size may be used to achieve the same eye box for the eye tracker as provided by a single transmitter and receiver of a second, larger size. The eye tracker transmitter(s) and/or receiver(s) may be sized to fit within a bezel region of a display of a head unit in some examples.

Another example provides for an in-vehicle computing system of a vehicle, the in-vehicle computing system including a camera, a light source, a display, a processor, and a storage device storing instructions executable to direct light from the light source to an eye of one or more occupants of the vehicle, the camera being located outside of a line of sight of the one or more occupants of the vehicle, receive, at the camera, light reflected from the eye of the one or more occupants of the vehicle, determine a gaze direction of each of the one or more occupants of the vehicle, and operate one or more of the in-vehicle computing system and another vehicle system based on the determined gaze direction. In a first example, the in-vehicle computing system further comprises an infrared filter configured to receive the light reflected from the eye of the one or more occupants of the vehicle. A second example optionally includes the first example, and further includes the in-vehicle computing system, wherein a plurality of light sources are provided linearly along an edge of a module housing the camera and the plurality of light sources, the camera mounted in line with each of the light sources, the edge being one or more of a top, bottom, left, or right edge of the module. A third example optionally includes one or both of the first and the second examples, and further includes the in-vehicle computing system wherein the display is mounted on a front face of the module, the light sources and camera further mounted on a same front face of the module along a top and/or bottom edge of the module. A fourth example optionally includes one or more of the first through the third examples, and further includes the in-vehicle computing system, further including a lens filter. A fifth example optionally includes one or more of the first through the fourth examples, and further includes the in-vehicle computing system, wherein the camera is positioned on an angled extension arm mounted to a rear surface of a housing, the housing including one or more electrical components of the in-vehicle computing system, and the display being positioned on an opposite side of the housing from the rear surface of the housing. A sixth example optionally includes one or more of the first through the fifth examples, and further includes the in-vehicle computing system, wherein the display is surrounded by a bezel, and wherein one or more of the camera and the light source is positioned within or behind the bezel. A seventh example optionally includes one or more of the first through the sixth examples, and further includes the in-vehicle computing system, wherein the in-vehicle computing system is positioned in a center console of a vehicle to a side of an instrument cluster positioned in front of a driver of the vehicle.

Another example provides for a method for operating an in-vehicle computing system of a vehicle, the method including generating, from a module mounted in the vehicle, light from an array of light sources mounted to the module, transmitting the generated light into a cabin of the vehicle, and receiving the light, as reflected off of one or more passengers of the vehicle, at a camera mounted in the module, one or more of the camera and the array of light sources being positioned outside a line of sight of the one or more passengers of the vehicle. In a first example, the method further includes determining a gaze direction of at least one of or both of a driver and a passenger of the vehicle, and adjusting an operating parameter of the vehicle based on the determined gaze direction(s). A second example optionally includes the first example, and further includes the method, wherein the received light is received at an infrared filter prior to being received at the camera. A third example optionally includes one or both of the first and the second examples, and further includes the method, wherein camera is positioned on an angled extension arm mounted to a rear surface of a housing of the module, the housing including one or more electrical components of the in-vehicle computing system, and a display being positioned on an opposite side of the housing from the rear surface of the housing. A fourth example optionally includes one or more of the first through the third examples, and further includes the method, wherein the in-vehicle computing system is positioned in a center console of a vehicle to a side of an instrument cluster positioned in front of a driver of the vehicle. A fifth example optionally includes one or more of the first through the fourth examples, and further includes the method, wherein the array of light sources are provided linearly along an edge of a module housing the camera and the plurality of light sources, the camera mounted in line with each of the light sources, the edge being one or more of a top, bottom, left, or right edge of the module, a housing of the module being rectangular shaped, and an at least partially transparent structure covering a surface of the housing of the module. A sixth example optionally includes one or more of the first through the fifth examples, and further includes the method, wherein the at least partially transparent structure extends past the surface of the housing of the module. A seventh example optionally includes one or more of the first through the sixth examples, and further includes the method, wherein transmitting the generated light from the array of light sources comprises transmitting light at an angle toward the one or more passengers of the vehicle.

The description of embodiments has been presented for purposes of illustration and description. Suitable modifications and variations to the embodiments may be performed in light of the above description or may be acquired from practicing the methods. For example, unless otherwise noted, one or more of the described methods may be performed by a suitable device and/or combination of devices, such as the in-vehicle computing system 109/200 and/or head unit 300 described with reference to FIGS. 1-3. The methods may be performed by executing stored instructions with one or more logic devices (e.g., processors) in combination with one or more additional hardware elements, such as storage devices, memory, hardware network interfaces/antennas, switches, actuators, clock circuits, etc. The described methods and associated actions may also be performed in various orders in addition to the order described in this application, in parallel, and/or simultaneously. The described systems are exemplary in nature, and may include additional elements and/or omit elements. The subject matter of the present disclosure includes all novel and non-obvious combinations and sub-combinations of the various systems and configurations, and other features, functions, and/or properties disclosed.

As used in this application, an element or step recited in the singular and proceeded with the word "a" or "an" should be understood as not excluding plural of said elements or steps, unless such exclusion is stated. Furthermore, references to "one embodiment" or "one example" of the present disclosure are not intended to be interpreted as excluding the existence of additional embodiments that also incorporate the recited features. The terms "first," "second," and "third," etc. are used merely as labels, and are not intended to impose numerical requirements or a particular positional order on their objects. The following claims particularly point out subject matter from the above disclosure that is regarded as novel and non-obvious.

The invention claimed is:

1. An in-vehicle computing system of a vehicle, the in-vehicle computing system comprising:
    a light source;
    a camera;
    a lens filter;
    a display;
    a processor; and
    a storage device storing instructions executable to:
        direct light from the light source to an eye of an occupant of the vehicle;
        receive, at the camera, light reflected from the eye of the occupant of the vehicle and transmitted through the lens filter;
        determine a gaze direction of the occupant of the vehicle based on the light received at the camera; and
        operate one or more of the in-vehicle computing system and another vehicle system based on the determined gaze direction,
    wherein the camera is positioned on an extension arm mounted to a rear surface of a housing, the extension arm positioning a field of view of the camera to have a predetermined orientation encompassing a seat for a driver of the vehicle.

2. The in-vehicle computing system of claim 1, wherein the camera extends above the rear surface of the housing; and wherein the extension arm is positioned at an angle with respect to at least one of a longitudinal axis of the housing, and a transverse axis perpendicular to the longitudinal axis.

3. The in-vehicle computing system of claim 2, wherein the field of view of the camera encompasses a region for eyes of a driver of the vehicle.

4. The in-vehicle computing system of claim 1, wherein the lens filter is an infrared filter.

5. The in-vehicle computing system of claim 1, wherein the display is mounted on a front face of a housing, and the light source and the camera are mounted on the front face of the housing along a top and/or bottom edge of the housing.

6. The in-vehicle computing system of claim 1, wherein the in-vehicle computing system is positioned in a center console of the vehicle to a side of an instrument cluster positioned in front of a driver of the vehicle.

7. The in-vehicle computing system of claim 1, wherein the light from the light source is directed to eyes of one or more occupants of the vehicle; wherein the light received at the camera is reflected from the eyes of the one or more occupants of the vehicle and transmitted through the lens filter; wherein gaze directions of the one or more occupants of the vehicle are determined based on the light received at the camera; and
    wherein the one or more of the in-vehicle computing system and another vehicle system are operated based on the determined gaze directions.

8. A head unit for an in-vehicle computing system of a vehicle, the head unit comprising:
    a light source mounted on a front face of a housing of the head unit;
    a camera positioned on an extension arm mounted to a rear surface of the housing and extending above the rear surface of the housing;
    a lens filter;
    a processor; and
    a storage device storing instructions executable to:
        direct light from the light source to eyes of one or more occupants of the vehicle;
        receive, at the camera, light reflected from the eyes of the one or more occupants of the vehicle and transmitted through the lens filter;
        determine a gaze direction of each of the one or more occupants of the vehicle; and
        operate one or more of the in-vehicle computing system and another vehicle system based on the determined gaze directions,
    wherein the extension arm is positioned at an angle with respect to at least one of a longitudinal axis of the housing, and a transverse axis perpendicular to the longitudinal axis.

9. The head unit of claim 8, wherein the extension arm positions a field of view of the camera to have a predetermined orientation encompassing a seat for a driver of the vehicle.

10. The head unit of claim 8, wherein the lens filter is an infrared filter configured to receive the light reflected from the eyes of the one or more occupants of the vehicle.

11. The head unit of claim 8, further comprising a display mounted on the front face of a housing, wherein the light source and the camera are mounted along a top and/or bottom edge of the housing.

12. The head unit of claim 11, wherein the display is surrounded by a bezel, and wherein one or more of the camera and the light source is positioned within or behind the bezel.

13. The head unit of claim 12, wherein the in-vehicle computing system is positioned in a center console of the vehicle to a side of an instrument cluster positioned in front of a driver of the vehicle.

14. A method for operating an in-vehicle computing system of a vehicle, the method comprising:
   generating light from an array of light sources mounted to a housing;
   transmitting the generated light into a cabin of the vehicle; and
   receiving the light, as reflected off of one or more passengers of the vehicle and transmitted through a lens filter, at a camera positioned on an extension arm mounted to a rear surface of the housing,
   wherein the extension arm is positioned at an angle with respect to at least one of a longitudinal axis of the housing and a transverse axis perpendicular to the longitudinal axis.

15. The method of claim 14, wherein a field of view of the camera encompasses a region for eyes of a driver of the vehicle.

16. The method of claim 14, wherein the method further comprises determining gaze directions of a driver of the vehicle, a passenger of the vehicle, or both; and adjusting an operating parameter of the vehicle based on the determined gaze directions.

17. The method of claim 14, wherein the lens filter is an infrared filter.

18. The method of claim 14, wherein the in-vehicle computing system is positioned in a center console of the vehicle to a side of an instrument cluster positioned in front of a driver of the vehicle.

19. The method of claim 14, wherein the array of light sources is provided linearly along an edge of the housing, the camera mounted in line with each of the light sources, the edge being one or more of a top, bottom, left, or right edge of the housing, the housing being rectangular shaped, and an at least partially transparent structure covering a surface of the housing.

20. The method of claim 14, wherein the extension arm is positioned at an approximately 70 degree angle with respect to the longitudinal axis, and is positioned at an approximately 20 degree angle with respect to the transverse axis.

* * * * *